US00PP26411P2

(12) United States Plant Patent
Meilland

(10) Patent No.: US PP26,411 P2
(45) Date of Patent: Feb. 16, 2016

(54) GRANDIFLORA ROSE PLANT NAMED 'MEISALIZA'

(50) Latin Name: *Rosa hybrida*
Varietal Denomination: Meisaliza

(71) Applicant: CP DELAWARE, INC., Wilmington, DE (US)

(72) Inventor: Alain A. Meilland, Antibes (FR)

(73) Assignee: CP DELAWARE, INC., Wilmington, DE (US)

( * ) Notice: Subject to any disclaimer, the term of this patent is extended or adjusted under 35 U.S.C. 154(b) by 24 days.

(21) Appl. No.: 14/121,067

(22) Filed: Jul. 28, 2014

(51) Int. Cl.
*A01H 5/02* (2006.01)

(52) U.S. Cl.
USPC ..... Plt./132

(58) Field of Classification Search
USPC ..... Plt./137, 132
CPC ..... A01H 5/0222; A01H 5/0216
See application file for complete search history.

*Primary Examiner* — Kent L Bell
(74) *Attorney, Agent, or Firm* — Buchanan Ingersoll & Rooney PC

(57) ABSTRACT

A new and distinct variety of Grandiflora rose plant is provided that abundantly and nearly continuously forms attractive very double white and pink blossoms which display a vervain fragrance. The vegetation is strong. An erect growth habit is displayed. The foliage is dense dark green with a glossy upper surface. The disease resistance is good, particularly with respect to *Oidium*. The plant is well suited for providing distinctive attractive ornamentation in the landscape.

1 Drawing Sheet

Botanical/commercial classification: *Rosa hybrida*/Grandiflora Rose Plant.

Varietal denomination: cv. Meisaliza.

SUMMARY OF THE INVENTION

The new variety of *Rosa hybrida* Grandiflora rose plant was created in France by artificial pollination wherein two parents were crossed which previously had been studied in the hope that they would contribute the desired characteristics. The female parent (i.e., the seed parent) was an unnamed and unreleased seedling (non-patented in the United States). The male parent (i.e., pollen parent) was the 'Meifaissel' variety (U.S. Plant Pat. No. 16,951).

The parentage of the new variety can be summarized as follows:

Unnamed Seedling×'Meifaissel'.

The seeds resulting from the above pollination were sown and small plants were obtained which were physically and biologically different from each other. Selective study resulted in the identification of a single plant of the new variety.

It was found that the new Grandiflora rose plant of the present invention:

(a) displays an erect growth habit with strong vegetation,
(b) forms attractive dense dark green foliage having a glossy upper surface,
(c) abundantly and nearly continuously forms attractive very double white and pink blossoms which display a vervain fragrance,
(d) displays good disease resistance particularly with respect to *Oidium*, and
(e) is well suited for providing distinctive attractive ornamentation in the landscape.

The white and pink blossom coloration contrasts nicely with the glossy dark green foliage.

The new variety well meets the needs of the horticultural industry and can be grown to advantage as colorful ornamentation in parks and gardens.

The new variety can be readily distinguished from its ancestors upon an inspection of the blossoms. More specifically, the female parent forms dissimilar yellow blossoms which lack fragrance, and the 'Meifaissel' variety forms pure white blossoms having a lesser number of petals.

The new variety also can be readily distinguished from the 'Hilaroma' variety (U.S. Plant Pat. No. 8,494, granted Dec. 14, 1993) and the 'Meibihars' variety (U.S. Plant Pat. No. 21,388, granted Oct. 19, 2010) through an inspection of the blossoms. More specifically, the blossoms of each comparative variety commonly possess a lesser number of petals than the new variety, the 'Hilaroma' displays dissimilar Naples Yellow strongly edged with Venetian Pink blossoms, and the 'Meibihars' variety displays dissimilar cream-colored blossoms margined with red.

The new variety has been found to undergo asexual propagation at Le Cannet des Maures, Var, France, by a number of routes, including budding, grafting, and the use of cuttings. Such asexual propagation by the above-mentioned techniques has shown that the characteristics of the new variety are stable and are strictly transmissible by such asexual propagation from one generation to another. Accordingly, the new variety undergoes asexual propagation in a true-to-type manner.

The new variety has been named 'Meisaliza'.

BRIEF DESCRIPTION OF THE PHOTOGRAPH

The accompanying photograph shows as nearly true as it is reasonably possible to make the same in a color illustration of this character, typical specimens of plant parts of the new variety. The rose plants of the new variety were approximately one year of age and were observed during June while budded on *Rosa laxa* understock and growing outdoors at Le Cannet des Maures, Var, France. Standard color information is included at the bottom of the photograph.

DETAILED BOTANICAL DESCRIPTION

Figures 1, 2, 3, 4, 5, 6, 7, 8, 9, 10, 11, 12, 13, 14:
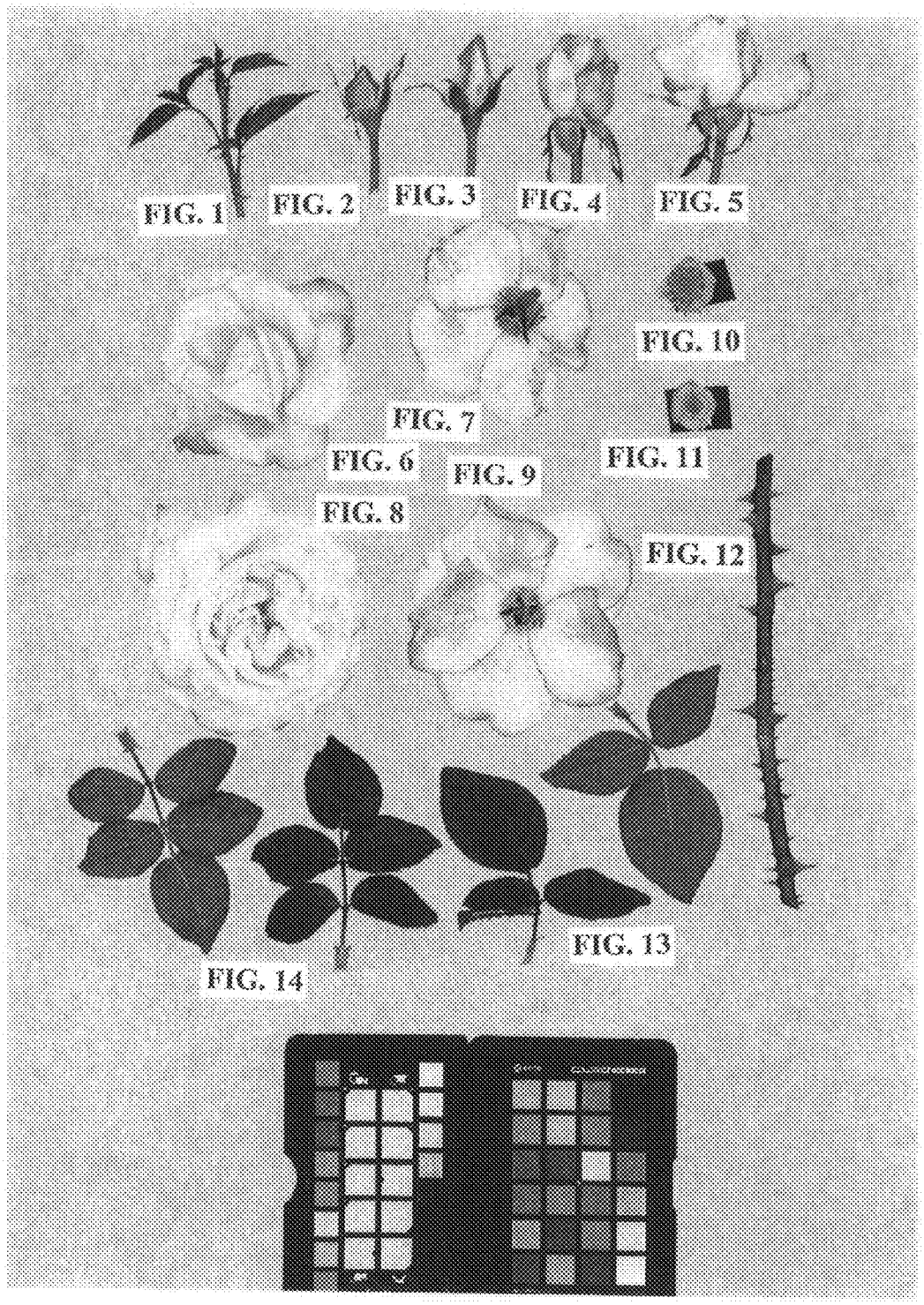
FIG. 1 illustrates a specimen of a young shoot.
FIG. 2 illustrates a specimen of a floral bud before the full opening of the sepals.
FIG. 3 illustrates a specimen of a floral bud at the full opening of the sepals.
FIG. 4 illustrates a specimen of a floral bud at the opening of the petals.
FIG. 5 illustrates a specimen of a flower in the course of opening.
FIG. 6 illustrates a specimen of an open flower—plan view—obverse.
FIG. 7 illustrates a specimen of an open flower—plan view—reverse.
FIG. 8 illustrates a specimen of a fully open flower—plan view—obverse.
FIG. 9 illustrates a specimen of a fully open flower—plan view—reverse.
FIG. 10 illustrates a specimen of a floral receptacle showing arrangement of the stamens and pistils.
FIG. 11 illustrates a specimen of a floral receptacle showing arrangement of the pistils (stamens removed)
FIG. 12 illustrates a specimen of a main branch.
FIG. 13 illustrates specimens of leaves with 3 leaflets—plan view—upper surface (left) and—under surface (right)
FIG. 14 illustrates specimens of leaves with 5 leaflets—plan view—upper surface (right) and—under surface (left).

The chart used in the identification of the colors is that of The Royal Horticultural Society (R.H.S. Colour Chart—1995 or equivalent) except where ordinary color terms are utilized. Common color terms are to be accorded their customary dictionary significance. The description is based upon the observation of plants of the new variety at an age of approximately one year during the month of June while budded on *Rosa laxa* understock and growing outdoors at Le Cannet des Maures, Var, France.

Class: Grandiflora.

Plant:

*Growth habit*.—Erect.

*Height*.—Commonly approximately 80 cm on average.

*Spread*.—Commonly approximately 60 cm on average.

Branches:

*Length*.—Approximately 80 cm on average.

*Diameter*.—Approximately 1 cm on average.

*Internode length*.—Approximately 3 to 3.5 cm on average.

*Color*.—Young stems: commonly near Yellow-Green Group 144A. Adult wood: commonly near Green Group 137A.

*Thorns*.—Configuration: slightly curved downwards on the upper surface and slightly concave on the under surface with an oval base. Quantity and size on young stems: commonly approximately 17 on average longer thorns having lengths of approximately 1.2 cm over a stem length of 10 cm, and approximately 48 on average small prickles having lengths of approximately 2 mm over a stem length of 10 cm. Quantity and size on adult stems: commonly approximately 18 on average longer thorns having lengths of approximately 1.3 cm over a stem length of 10 cm, and approximately 37 on average small prickles having lengths of approximately 2 to 5 mm over a stem length of 10 cm. Color on young stems: near Greyed-Purple Group 181B for longer thorns, and near Greyed-Purple Group 184A for small prickles. Color on adult stems: near Greyed-Purple Group 184A for both longer thorns and small prickles.

Leaves:

*Overall appearance*.—Dense dark green.

*Length*.—Approximately 11 to 12 cm on average for a five-leaflet leaf.

*Width*.—Approximately 9 to 10 cm on average for a five-leaflet leaf.

*Leaflets*.—Shape: generally oval. Number: 3, and most often 5 and 7. Apex: acuminate. Base: obtuse. Serration: slightly denticulate, small and single. Texture: firm, and leathery, and glossy on the upper surface. Length: commonly approximately 7.5 to 8 cm on average for a terminal leaflet. Width: commonly approximately 4.5 to 5 cm on average for a terminal leaflet. Color (young foliage): near Green Group 137A on the upper surface, and near Green Group 137C on the under surface. Color (adult foliage): near Green Group 139A on the upper surface, and Yellow-Green Group 146A on the under surface.

*Petiole*.—Length: commonly approximately 4.5 cm on average. Diameter: approximately 1 to 2 mm on average. Texture: non-glandular on the upper surface and commonly with a few prickles on the under surface. Color: near Yellow-Green Group 148A on the upper surface, and near Yellow-Green Group 147B on the under surface.

*Rachis*.—Length: approximately 5 to 6 cm on average. Diameter: approximately 1 mm on average. Color: near Green Group 137A suffused with Greyed-Purple Group 178D on the upper surface, and near Green Group 137C on the under surface.

*Stipules*.—General appearance: adnate, pectinate, and rather broad. Size: commonly approximately 2 cm in length on average, and approximately 7 mm in width on average. Color: near Yellow-Green Group 146B on both surfaces.

Inflorescence:

*Number of flowers*.—Commonly approximately 1 to 3 blossoms per stem.

*Peduncle*.—Glandular, commonly approximately 7.5 cm in length on average, approximately 5 mm in diameter on average, commonly somewhat glandular, and near Yellow-Green Group 146C in coloration.

*Sepals*.—Shape: longish and somewhat narrow, and initially borne upright at the base. Texture: tomentose on upper surface, and smooth on the under surface. Apex: pointed. Size: approximately 2.6 cm in length on average, and approximately 1.2 cm in width on average at the base. Extensions: commonly up to approximately 1.5 cm in length. Color: near Yellow-Green Group 146C on the upper surface, and near Green Group 143B to Yellow-Green Group 144B on the under surface.

*Buds*.—Shape: generally conical and medium in size. Length: approximately 2.9 cm on average. Width: approximately 2.4 cm at the widest point on average.

Color: as the calyx breaks: on the upper surface near Yellow-White Group 158B suffused and slightly margined with near Red-Purple Group 74A and 74D, and on the under surface near Yellow-White Group 158B slightly margined with near Red-Purple Group 74A and 74B.

*Flower*.—Diameter: approximately 11 to 12 cm on average when fully open. Depth: approximately 7 to 8 cm on average. Shape: cup-shaped. Color (in course of opening): Upper side: external petals are near White Group 155A and slightly suffused and margined with near Red-Purple Group 68A and 68B, internal petals are near White Group 155A, and with a spot of near Yellow Group 2D at the base. Under side: external petals are near White Group 155A and very slightly suffused and margined with Red-Purple Group 68A and 68B, internal petals are near White Group 155A, and with a spot of near Yellow Group 2B at the base. Color (when open): Upper side: external petals are near White Group 155A slightly suffused and margined with near Red-Purple Group 68A and 68B, and with a spot of near Yellow Group 2D at the base. Under side: external petals are near White Group 155A very slightly suffused and margined with near Red-Purple Group 68A and 68B, internal petals are near White Group 155A, and with a spot of Yellow Group 2B at the base. Fragrance: resembles strong vervain. Longevity: approximately 10 to 12 days on average on the plant depending on environmental conditions with the plant being intended primarily for garden usage. Petal number: commonly approximately 58 to 63 on average under normal growing conditions. Petal shape: commonly display a rounded tip and a rounded base. Petal arrangement: imbricated and commonly without petaloids. Petal margins: entire. Petal texture: relatively soft. Petal length: commonly approximately 5.3 cm on average. Petal width: commonly approximately 5.2 cm on average. Petal drop: good with the petals commonly detaching cleanly before drying. Stamen number: commonly approximately 134 on average. Anthers: arranged regularly around the styles, commonly approximately 2 mm in length on average, approximately 1 mm in diameter on average, and near Yellow Group 11C edged with Red Group 47D in coloration. Filaments: commonly approximately 6 mm in length on average, and near Red Group 47D in coloration. Pistils: commonly approximately 97 on average. Styles: commonly approximately 1 mm in length on average, and near Yellow-Green Group 147C in coloration. Stigmas: commonly approximately 7 to 9 mm in size on average and near Yellow-Green Group 150D in coloration. Hips: none encountered during observations to date.

Development:

*Vegetation*.—Strong.

*Blooming*.—Early season, very abundant and nearly continuous.

*Tolerance to diseases*.—Good, particularly with respect to *Oidium*.

I claim:

1. A new and distinct Grandiflora rose plant characterized by the following characteristics:

(a) displays an erect growth habit with strong vegetation, (b) forms attractive dense dark green foliage having a glossy upper surface, (c) abundantly and nearly continuously forms attractive very double white and pink blossoms which display a vervain fragrance, (d) displays good disease resistance particularly with respect to *Oidium*, and (e) is well suited for providing distinctive attractive ornamentation in the landscape;

substantially as shown and described.

* * * * *